United States Patent [19]

Chackalamannil

[11] Patent Number: 5,089,609
[45] Date of Patent: Feb. 18, 1992

[54] 4-BENZOYL AZETIDINONES

[75] Inventor: Samuel Chackalamannil, W. Paterson, N.J.

[73] Assignee: Schering Corporation, Kenilworth, N.J.

[21] Appl. No.: 621,158

[22] Filed: Nov. 30, 1990

Related U.S. Application Data

[62] Division of Ser. No. 496,468, Mar. 20, 1990, Pat. No. 5,008,404, which is a division of Ser. No. 227,084, Nov. 28, 1988, Pat. No. 4,963,670, which is a division of Ser. No. 127,844, Dec. 2, 1987, Pat. No. 4,827,006, which is a division of Ser. No. 839,307, Mar. 13, 1986, Pat. No. 4,740,595.

[51] Int. Cl.$^5$ .......................... C07D 205/08
[52] U.S. Cl. .................... 540/200
[58] Field of Search ........................ 540/200

[56] References Cited

U.S. PATENT DOCUMENTS 4,574,153  3/1986  Kronethal et al. ............... 544/363
4,614,414  9/1986  Ernest et al. ..................... 540/359

FOREIGN PATENT DOCUMENTS 0181831  5/1986  European Pat. Off. .

OTHER PUBLICATIONS

Chakalamannil, Chem Abs 108, 131415k (1987).
Yanagisawa et al., Tetrahedron Letters, vol. 24, No. 10, pp. 1037–1040 (1983).
Izumiya, Bull, Chem., Soc. Japan, vol. 26, pp. 53–56 (1953).
Kronenthal et al., J. Org. Chem., 47, pp. 2765–2768 (1982).
Huffman et al., J.A.C.S. 99, 2352 (1977)
Dornow et al., Berichte, vol. 88, pp. 1267–1275 (1955) (See Also Chem. Abstract vol. 50, No. 13775i).
Hanessian et al., J. Am. Chem. Soc., 1985, 107, pp. 1438–1439.
Maruyama et al., Tetrahedron Letters, vol. 26, No. 37, pp. 4521–4522 (1985).
Sankyo Chemical Abstract, No. 103: 160299c (1985).
S.S. Pharmaceutical Chemical Abstract 102: 149103t (1985).
Sundberg et al., J. Org. Chem., vol. 38, No. 19, pp. 3050897511 324-3330 (1973).
Kalvoda Chemical Abstract 106:4751a.
Dornow Chemical Abstract, vol. 50, No. 13775i.

*Primary Examiner*—Mark L. Berch
*Attorney, Agent, or Firm*—Matthew Boxer; James R. Nelson; Henry C. Jeanette

[57] ABSTRACT

Compounds of the formula

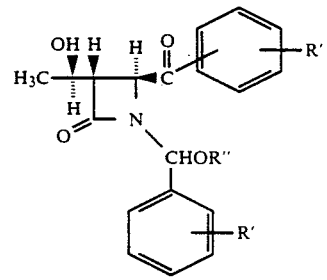

wherein each R' is independently hydrogen, one, two or three of halogen, lower alkyl or lower alkoxy and R" is methyl, ethyl, allyl or a phenyl, are described. These compounds are useful as intermediates in preparing penems and carbapenems.

2 Claims, No Drawings

4-BENZOYL AZETIDINONES

This is a division of application Ser. No. 07/496,468, filed Mar. 20, 1990 now U.S. Pat. No. 5,008,404; which in turn is a division of application Ser. No. 07/227,084, filed Nov. 28, 1988, now U.S. Pat. No. 4,963,670; which in turn is a division of application Ser. No. 07/127,844 filed Dec. 2, 1987, now U.S. Pat. No. 4,827,006; which in turn is a division of application Ser. No. 06/839,307 filed Mar. 13, 1986, now U.S. Pat. No. 4,740,595.

BACKGROUND

This invention relates to an improvement in a multi-step stereospecific process for producing azetidinones which are useful as intermediates for preparing penems and carbapenems. More particularly, this invention relates to an improvement in the stereospecific multi-step process in which L-threonine is converted to an epoxyamide containing a specific nitrogen protecting group, lower alkoxyphenylmethyl, preferably ethoxyphenylmethyl, cyclizing to form an azetidinone, then readily removing the protecting group under mild acidic conditions.

In the multistep processes heretofore utilized L-threonine is converted to (2S, 3R)-2-bromo-3-hydroxybutyric acid as disclosed for example in Yanagisawa, et. al., Tetrahedron Letter 24 No. 10, 1037 (1984) or Izumiya, Bull. Chem. Soc. Japan, 26, 53 (1953). The (2S, 3R)-2-bromo-3-hydroxybutyric acid is converted to an epoxyamide. The epoxyamide is converted, by ring closure to an azetidinone in which the nitrogen is protected by a para-methoxyphenyl or a 2,4-dimethoxybenzyl group. The former N-protecting group can be removed by the method disclosed in Kronenthal et. al., J. Org. Chem., 47, 2765 (1982), i.e. by use of ceric ammonium nitrate. Another means of removing that N-protecting group is by ozonolysis in ethyl acetate. The 2,4-dimethoxybenzyl group can be removed by use of potassium persulfate-dipotassium hydrogen phosphate in acetonitrile-water as disclosed by Huffman et. al. J.A.C.S. 99, 2352 (1977). These prior art deprotection processes are difficult and expensive to conduct. There is thus a need for a nitrogen protecting group which is readily removable under relatively mild conditions producing high yields.

SUMMARY OF THE INVENTION

This invention provides an improved process step in a multistep process for producing azetidinone intermediates for penems and carbapenems. More particularly, this invention provides the steps of producing azetidinones represented by the formula

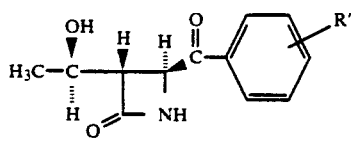

wherein $R^1$ is independently hydrogen, one, two, or three of halogen, lower alkyl or lower alkoxy, preferably hydrogen, from L-(-)-threonine in a multistep process utilizing as an N-protecting group lower alkoxyphenylmethyl, aromatic oxyphenylmethyl or alkenyloxyphenylmethyl, preferably ethoxyphenylmethyl.

There are two routes to produce the compound of formula I. The first, most preferred route, designated Reaction Scheme A comprises the steps (a) reacting L-(-)-threonine with sodium bromide and sodium nitrite to produce a compound represented by the formula

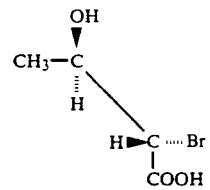

(b) reacting the compound produced in Step (a) with acetylchloride followed by reaction with oxalyl chloride to produce a compound represented by the formula

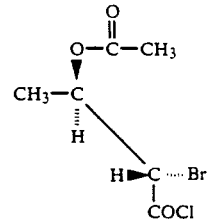

(c) reacting the compound produced in Step (b) with a compound represented by the formula

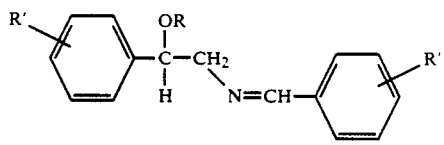

wherein R is —Si(CH$_3$)$_3$ or —Si(CH$_3$)$_2$ t—C$_4$H$_9$ and R' is as defined for compound I, followed by reaction with anhydrous alcohol, e.g. methanol, phenol, allylalcohol or ethanol, preferably ethanol, to produce a compound represented by the formula

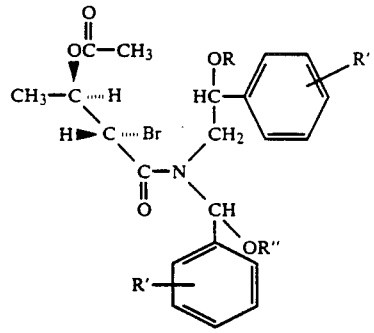

wherein R is hydrogen, —Si(CH$_3$)$_3$ or —Si(CH$_3$)$_2$—t—C$_4$H$_9$, R' is as defined for compound I and R" is methyl, ethyl, allyl, substituted or unsubstituted phenyl wherein the substituents are R', preferably ethyl (d) reacting the compound produced in Step (c) where R is —Si(CH$_3$)$_3$ with anhydrous potassium carbonate to produce a compound represented by the formula

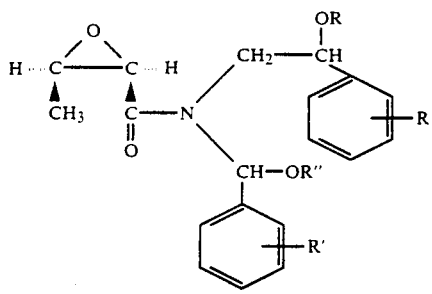

wherein R is hydrogen, or —Si(CH₃)₃, R' is as defined for compound I and R" is as defined for compound B (e) reacting the compound produced in step (d) with pyridinium chlorochromate and anhydrous sodium acetate to produce a compound represented by the formula

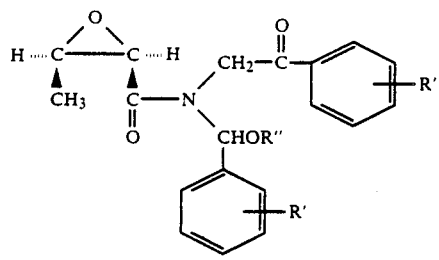

wherein R' and R" are as hereinabove defined (f) cyclizing the compound produced in step (e) by reacting with lithium hexamethyldisilazide to produce a compound represented by the formula

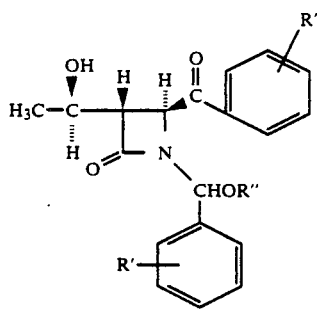

wherein R' and R" are as hereinabove defined (g) deprotecting the nitrogen of the compound produced in step (f) by reacting with a dilute inorganic acid to produce a compound represented by the formula

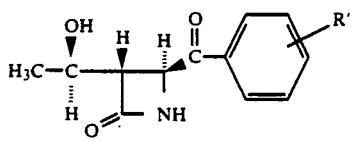

wherein R' is as defined hereinabove

A second route designated Reaction Scheme B comprises the steps of (a) reacting a compound represented by the formula

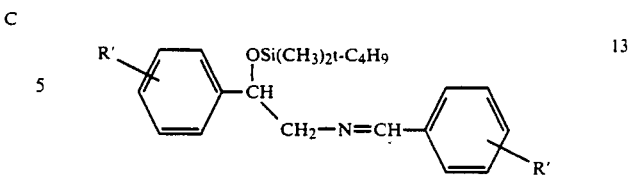

with a compound represented by the formula

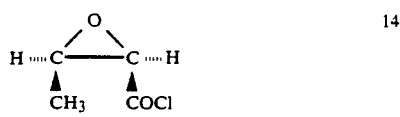

and an anhydrous alcohol, e.g. methanol, ethanol, allyl alcohol or phenol, preferably ethanol, to produce a compound represented by the formula

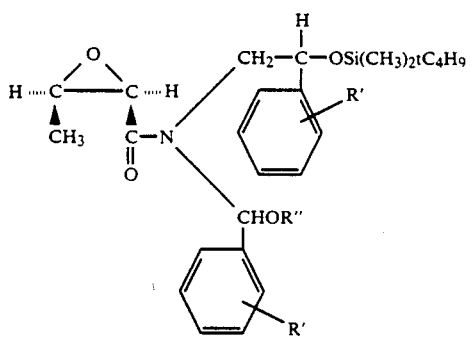

wherein R' and R" are as defined hereinabove (b) reacting the compound produced in step (a) with tetra-n-butylammonium fluoride to produce a compound represented by the formula

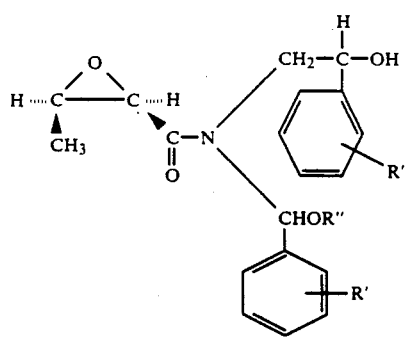

wherein R' and R" are as hereinabove defined (c) reacting the compound produced in step (b) with pyridinium-chlorochromate to produce a compound represented by the formula

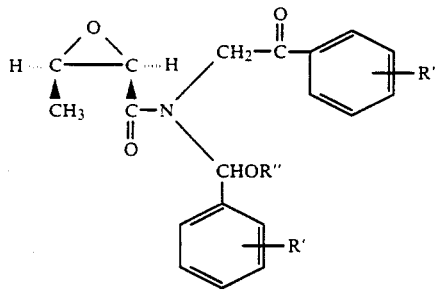

wherein R' and R" are as hereinabove defined.

The compound produced in step (c) is converted to a compound of formula I as in steps (f) and (g) of Reaction Scheme A.

As used herein "lower alkyl" alone or in groups containing a lower alkyl moiety e.g. "lower alkoxy" means straight or branched chain alkyl groups having from 1 to 7 carbon atoms, e.g. methyl, ethyl, propyl, isopropyl, butyl, t-butyl, pentyl, hexyl, neopentyl, dimethyl butyl and the like. Preferred is ethyl.

"Lower alkenyl" means straight or branched chain alkenyl groups having from 3 to 7 carbon atoms, e.g. allyl, 2-butenyl, 3-butenyl and the like, preferred is allyl.

"Inert organic solvent" means an organic solvent which is non-reactive under the reaction conditions, e.g. tetrahydrofuran (THF), methylene chloride, lower alkanols, preferably methanol or ethanol, and the like.

"Halogen" means chlorine or bromine, preferably chlorine.

"Readily removable nitrogen protecting group" as used herein means a nitrogen protecting group which is removed from the azetidinone nitrogen under mild acidic conditions which do not affect other parts of the azetidinone molecule and do not cause any stereoisomeric changes. The readily removable nitrogen protecting groups contemplated by this invention are lower alkoxy phenyl methyl groups, preferably ethoxy phenyl methyl.

"Dilute inorganic acid" means, about 0.5 to 2.0 molar hydrochloric acid, sulfuric acid or nitric acid, preferably one molar.

"Aromatic" means phenyl or benzyl, either substituted or unsubstituted wherein the substituents are R'.

DETAILED DESCRIPTION

The process of this invention provides novel intermediates containing specific readily removable nitrogen protecting groups as depicted in the following structural formulas.

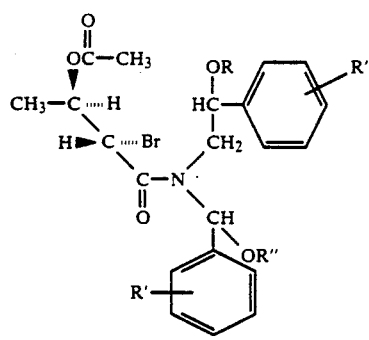

wherein R is —Si(CH₃)₃ or —Si(CH₃)₂ t—C₄H₉, R' is as defined for compound I and R" is as defined hereinabove for compound B

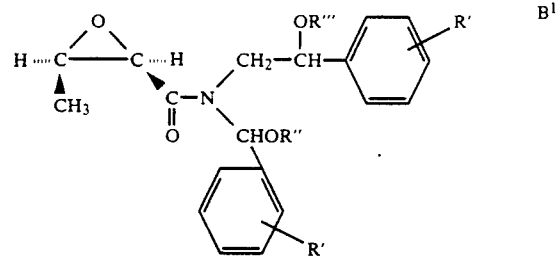

wherein R'" is hydrogen, —Si(CH₃)₃ or —Si(CH₃)₂ t—C₄H₉, R' and R" are as defined hereinabove.

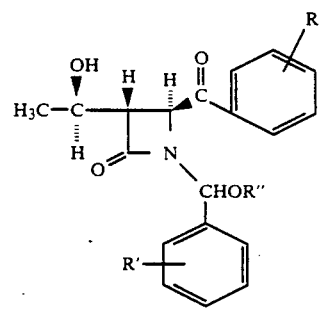

wherein R' and R" are as hereinabove defined, a preferred compound is wherein R' is hydrogen and R" is ethyl and

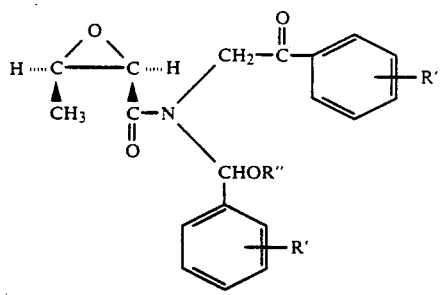

wherein R' and R" are as hereinabove defined. A preferred compound is wherein R' is hydrogen and R" is ethyl.

The above novel intermediates are useful for producing an azetidinone represented by the formula

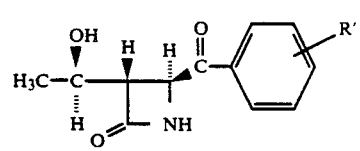

wherein R' is as defined hereinabove. A preferred compound is wherein R' is hydrogen. The azetidinones of formula I are intermediates for producing penems and carbapenems, and are prepared by two different Reaction Schemes. In one Reaction Scheme, designated Scheme A, wherein the preferred compounds are used for illustration, L-threonine is converted to an epoxyamide which is converted to an azetidinone, then deprotected at the nitrogen, as follows:
Scheme A
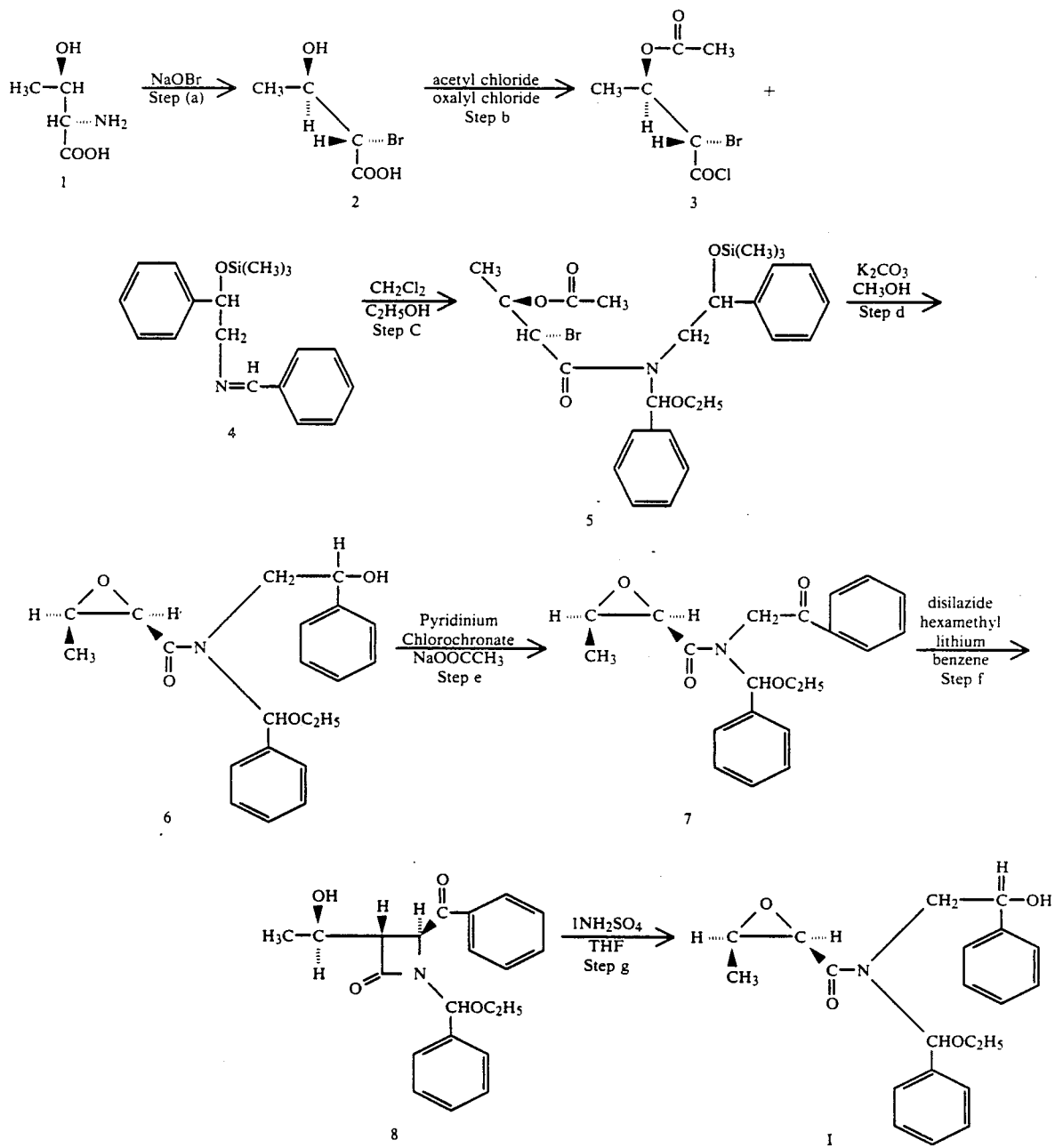
Compound 4, used in Reaction Scheme A, is prepared as follows:
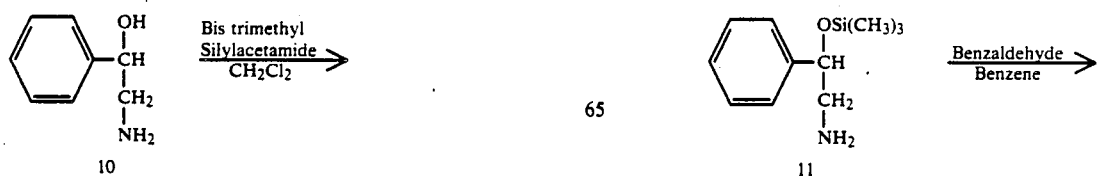

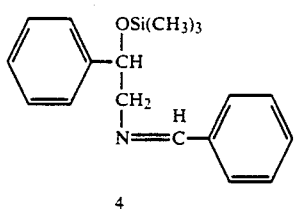

4

In Step (a) of Reaction Scheme A (Step Aa) L-(-)-threonine is converted to (2S, 3R) 2-bromo-3-hydroxybutyric acid by reaction with an alkali metal bromide, e.g., potassium or sodium bromide and an alkali metal nitrite, e.g., potassium or sodium nitrite, in acidic aqueous medium, preferably sulfuric acid at about 5° to 10° C. until the reaction is complete, i.e., about 30 minutes.

In Step Ab (2S,3R)-2-bromo-3-acetoxy-butyryl chloride is prepared by the reaction of (2S,3R)-2-bromo-3-hydroxy-butyric acid with acetyl chloride, then the reaction mixture is reacted with oxalyl chloride or thionyl chloride in an inert solvent, e.g. toluene, at cold temperatures, e.g. about 0° to 10° C., under an inert atmosphere, e.g., nitrogen.

In Step Ac (2S,3R)-2-bromo-3-acetoxy-butyryl chloride is reacted with 1-phenyl-1-trimethylsiloxyethyl-2-benzaldimine in an inert solvent, e.g. dichloromethane, at cold temperatures, e.g. about 0° to 10° C. Then an anhydrous alcohol, e.g. ethanol, methanol, substituted or unsubstituted phenol or allyl alcohol, is added, followed by an organic base, e.g., pyridine or triethylamine, to neutralize the hydrogen chloride generated and the reaction is continued at room temperature, e.g. about 25° C. The resulting product when ethanol is used, (2S,3R)-[N-(ethoxyphenylmethyl)-N-(2-phenyl-2-trimethyl silyloxy ethyl)]-2-bromo-3 acetoxybutyramide is recovered.

In Step Ad the product of Step Ac is reacted with anhydrous potassium carbonate at room temperature to produce N-(ethoxyphenylmethyl)-N-(2-hydroxy-2-phenylethyl) glycidamide.

In Step Ae the hydroxy group is oxidized to a ketone group by reacting the compound produced in Step Ad with a mixture of pyridinium chlorochromate and anhydrous sodium acetate. The reaction is conducted at room temperature until completed in about 1.5 hours as evidenced by thin layer chromatography (TLC).

In Step Af the compound produced in Step Ae is cyclized to the azetidinone, i.e. (3S,4S)-1-(ethoxyphenylmethyl)-3-(1R-hydroxyethyl)-4-benzoyl azetidin-2-one, by reaction with a strong base, preferably lithium hexamethyldisilazide in an inert organic solvent, e.g. hexanes, at about 8°-12° C. until complete in about 1.5 hours as evidenced by TLC.

In Step Ag (3S,4S)-3-(1R-hydroxyethyl)-4-benzoyl-2-azetidinone is prepared from the compound of Step Af by removing the nitrogen protecting group with dilute sulfuric acid in an inert organic solvent, e.g. THF, at room temperature for about 24 hours. The reaction mixture is neutralized with sodium bicarbonate and the product recovered in high yield based on the compound produced in Step Af.

The 1-phenyl-1-trimethylsiloxy-2-benzaldimine intermediate utilized in Step Ac is prepared by reacting the appropriately substituted 2-amino-1-phenylethanol, with bis(trimethylsilyl)acetamide at room temperature for about 3 hours in an inert organic solvent, e.g. dichloromethane. The product thus obtained, the appropriately substituted 2-amino-1-phenyl-1-trimethylsiloxyethane, is reacted with the appropriately substituted benzaldehyde for a short time, e.g. about 2 minutes, then an inert organic solvent, e.g. benzene, is added and water, which is liberated in the reaction, is removed with anhydrous magnesium sulfate.

In the following Reaction Scheme B, a compound of formula I is prepared by reacting an analog of compound 4, i.e. wherein the trimethylsilyl group is replaced by a t-butyl dimethylsilyl group, with an oxirane butyryl chloride to produce the compound analogous to compound 6 of Reaction Scheme A, i.e. wherein the hydrogen is replaced by a t-butyl dimethyl silyl group. Subsequent deprotection of the hydroxy group to obtain compound 6 and following the remaining steps of Reaction Scheme A results in Compound I, as follows, using the preferred compounds for illustrative purposes:

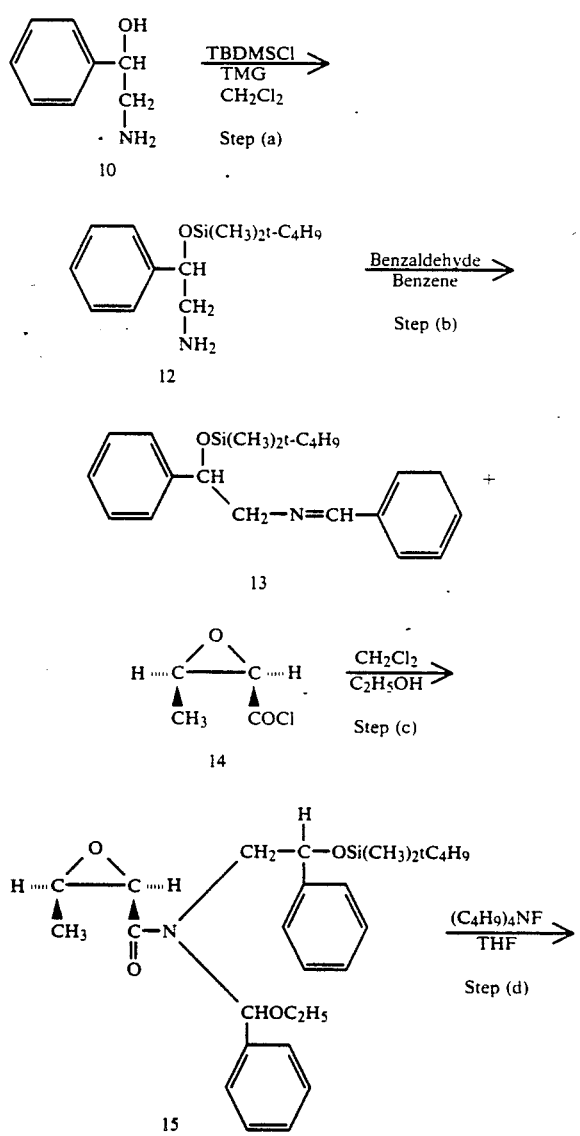

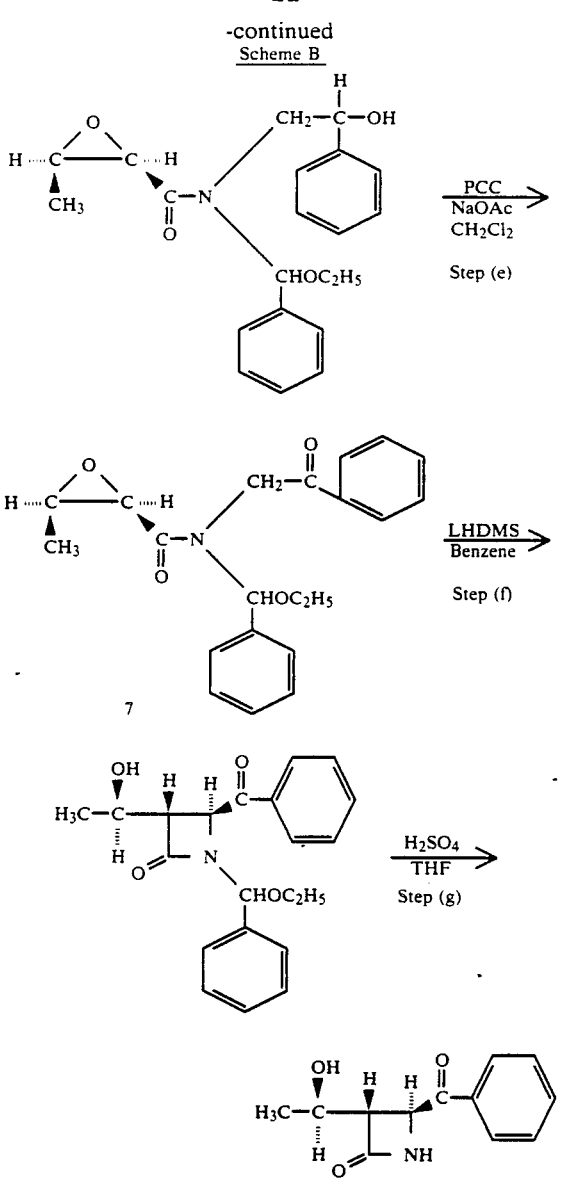

-continued
Scheme B

Step (e)

Step (f)

Step (g)

In Step a of Reaction Scheme B, i.e. Step Ba, 2-amino-1-phenylethanol [prepared by the method of Dornow, Ber. 88, 1267 (1955)] is reacted in an inert organic solvent, e.g. dichloromethane, with tertiary butyl dimethylsilyl chloride followed by tetramethyl guanidine at room temperature for about 15 minutes. The reaction is quenched with water to yield 2-phenyl-2-tert butyl-dimethylsiloxy-1-ethylamine.

In Step Bb, the product of Step Ba is reacted with benzaldehyde. Following addition of an inert organic solvent, e.g. benzene, the water liberated in the reaction is taken up with magnesium sulfate to yield 1-phenyl-1-tertiary butyl-dimethylsiloxy 2-benzaldimine.

In Step Bc, (2R, 3R)-2,3-oxirane butyryl chloride is reacted with the product of Step Bb at about 0°-10° C. in an inert organic solvent, e.g. dichloromethane. After about 30 minutes, an organic base, e.g. triethylamine or pyridine is added. An anhydrous alcohol, e.g. methanol, ethanol, phenol or allyl alcohol, preferably ethanol, is added to form the appropriate ether substituent on the phenylmethy group. When the preferred ethanol is used, the product, (2R,3R)-N-ethoxyphenyl-methyl-N-phenyl-tert butyl dimethylsiloxy-b-methylglycidamide, is made and recovered in high yields.

In Step Bd, the compound produced in Step Bc is deprotected at the hydroxy group by reacting the compound with tetra n-butylammonium fluoride in an inert organic solvent, e.g. THF, at room temperature until the reaction is complete in about 12 hours as evidenced by TLC.

In Step Be the compound produced in Step Bd is oxidized to the ketone by reaction with pyridinium chlorochromate and sodium acetate in an inert organic solvent, e.g. dichloromethane, for about 1 to 2 hours at room temperature.

The compound from Step Be is converted to compound I in the same manner as in Steps Af and Ag.

The intermediate reactant (2R,3R)-2,3 oxirane butyrylchloride is prepared by reaction of (2S,3R)-2-bromo-3-hydroxybutyric acid and potassium hydroxide in absolute ethanol, followed by thionyl chloride in THF.

The following Examples illustrate the invention:

EXAMPLE 1

(2S,3R)-2-bromo-3-acetoxy-butyryl chloride

Acetyl chloride (6.82 g, 86.88 mmole) was added dropwise to (2S, 3R)-2-bromo-3-hydroxybutyric acid (neat) with stirring. The reaction mixture was cooled in a bath at 5° C. as exotherm began. After completion of addition, the cooling bath was removed. After 45 minutes the mixture was heated at 45°-50° C. for 1.5 hours. Heating was discontinued and 10 mL toluene was added. The mixture was cooled in an ice bath and oxalyl chloride (11.4 80 g, 90.44 mmole) was added dropwise. After completion of addition, the mixture was allowed to warm to room temperature then heated at reflux for 30 minutes. Toluene and excess of reagents were removed by fractional distillation. The residue was subjected to bulb-to-bulb distillation at 80°-90° C. under high vacuum (1 mm/Hg) to yield the title compound.

$^1$H NMR (200 MHz, CDCl$_3$) w 1.44 (d, J=6.0 Hz, 3H), 2.11 (s, 3H), 4.67 (d, J=6.0 Hz,1H), 5.41 (m, 1H); IR (neat) 1810, 1790, 1740 cm$^{-1}$.

EXAMPLE 2

(2R,3R)-N-(Ethoxyphenylmethyl)-N-(2-oxo-2-phenylethyl)-2,3-oxiranebutyramide (a) 2-phenyl-2-trimethylsiloxyethylamine To a solution of 2-amino-1-phenylethanol (5.104 g, 37.21 mmole) in 25 mL dichloromethane was added bis(trimthylsily)acetamide (6.122 g, 31.10 mmole). The reaction mixture was stirred at room temperature for 3 hours. The mixture was diluted with dichloromethane (150 mL) and washed with water (2×100 mL). The organic phase was dried over magnesium sulfate and concentrated in vacuo. The 2-phenyl-2-trimethylsiloxyethylamine thus obtained was directly used for the next step.

(b) 1-phenyl-1-trimethylsiloxy-2-benzaldimine

The crude product from step (a) herein was mixed with benzaldehyde (4.452 g, 42.00 mmole). The reaction mixture was stirred for 2 minutes and benzene (50 mL) was added. The water liberated was removed by addition of anhydrous magnesium sulfate. The mixture was filtered, and the residue was washed with benzene (2×10 mL). The solvent was removed under reduced pressure. The product, 1-phenyl-1-trimethylsiloxy-2- benzaldimine, was subjected to high vacuum for 2 hours and used immediately for the next step.

(c) (2S,3R)-N-(ethoxyphenylmethyl)-N-(2-trimethylsiloxy-2-phenylethyl)-2-bromo-3-acetoxybutyramide To a stirred solution of the compound produced in step (b) herein in 24 mL dichloromethane, kept cooled in an ice bath, was added a solution of the compound produced in Example 1 (9.037 g, 37.14 mmole) in 25 mL dichloromethane. After completion of addition, cooling was discontinued. The reaction mixture was stirred for 25 minutes and triethylamine (5.420 g, 53.56 mmole) was added, followed after 2 minutes by anhydrous ethanol (6.920 g, 150.20 mmole). The reaction mixture was stirred at room temperature for 1.5 hours. To this was added dichloromethane (25 mL) and water (50 mL). Layers were separated and the aqueous phase was extracted with dichloromethane (3×30 mL). Combined organic phases were washed with water (150 mL), dried over magnesium sulfate, and concentrated in vacuo to give the title compound. In this step, if methanol, allyl alcohol or a phenol is used in place of ethanol, then the corresponding etherified phenylmethyl substituent is formed. Then following the remaining steps of this Example 2 yields the correspondingly substituted compound as the final product.

(d) (2R,3R)-N-(ethoxyphenylmethyl)-N-(2-phenylethan-2-ol)-2,3-oxirane butyramide To a solution of 8.900 g (16.18 mmole) of the above crude product in 55 mL methanol was added anhydrous potassium carbonate (2.23 g, 16.13 mmole). The reaction mixture was stirred at room temperature for 18 hours. The suspensions were filtered and the filtrate concentrated in vacuo. The residue was dissolved in dichloromethane and washed with water (100 mL). The aqueous phase was extracted with dichloromethane (75 mL). Combined organic phases were washed with water (100 mL), dried over magnesium sulfate and concentrated under reduced pressure to give the crude title compound.

(e) (2R,3R)-N-(ethoxyphenylmethyl)-N-(2-oxo-2-phenylethyl)2,3-oxirane butyramide To a solution of the compound produced in step (d) herein in dichloromethane (25 mL) was added a powdered mixture of pyridiniumchlorochromate (13.790 g, 63.97 mmole) and anhydrous sodium acetate (3.080 g, 37.55 mmole). The suspension was stirred at room temperature for 1.5 hr. The reaction mixture was diluted with dichloromethane (50 mL), filtered, and the filtrate concentrated in vacuo. The residue was subjected to chromatography on silica gel eluting with 35% ethyl acetate in hexanes to give the title compound.

$^1$H NMR (200 MHz, CDCl$_3$) δ 1.13–1.59 (m, 6H), 3.20–5.00 (m, 6H), 6.57 (s, 0.2H), 6.65 (s, 0.2H), 7.02 (s, 0.3H), 7.06 (s, 0.3H), 7.20–7.95 (m, 10H); IR (neat) 1700, 1665 cm$^{-1}$; MS (CI, m/e) 352, 308, 224, 146, 134.

EXAMPLE 3

(3S,4S)-1-(Ethoxyphenylmethyl)-3-[1R-hydroxethyl]-4-benzoyl-2-azetidinone).

To a solution of the compound produced in Example 2 (1.250 g, 3.54 mmole) in 10 mL dry benzene, cooled in a bath at 8° C., was added a solution of lithium hexamethyldisilazide in hexanes (5.3 mL, 5.3 mmole). The reaction mixture was stirred at 8°–12° C. for 1.5 hr. and 8 mL of 20% aqueous solution citric acid was added, followed by 20 mL ethyl acetate. Layers were separated and the organic phase washed with ethyl acetate (15 mL). The organic phases were combined, dried over magnesium sulfate, and concentrated under reduced pressure. The residue was subjected to chromatography on silica gel using 30% ethyl acetate in hexanes to give the title compound.

$^1$H NMR (200 MHz, CDCl$_3$) δ 1.18–1.38 (m, 6H), 3.32 (dd, J=6.0 Hz, 2.5 Hz, 1H), 3.6–4.04 (m, 2H), 4.30–4.42 (m, 1H), 5.25 (d, J=2.5 Hz, 1H), 6.07 (s, 1H), 7.04–7.80 (m, 10H); 1R (neat) 3400–3600 (broad), 1760, 1750, 1690 cm$^{-1}$; MS (FAB, m/e) 352, 308, 290, 264, 224, 203, 159, 135.

EXAMPLE 4

(3S,4S)-3-(1R-Hydroxyethyl)-4-benzoyl-2-azetidinone

To a solution of the compound produced in Example 3 (890 mg, 2.52 mmole) in 2 mL tetrahydrofuran was added 1 mL of 1N H$_2$SO$_4$. The reaction mixture was stirred at room temperature for 24 hours. To this was added 10 mL dichloromethane and 10 mL water. Solid sodium bicarbonate was added until the aqueous phase was neutral. Layers were separated and the aqueous phase was extracted with ethyl acetate (10 mL). Combined organic phases were dried over magnesium sulfate and concentrated in vacuo. The residue was subjected to chromatography over silica gel using 60% ethyl acetate in hexanes to yield the title compound which was crystallized from dichloromethane-ether (mp, 131°–132° C.) in a 74% yield based on the starting material.

$^1$H NMR (200 MHz, CDCl$_3$) δ 1.38 (d, J=6.3 Hz, 3H), 2.15 (br S, 1H), 3.25 (m, 1H), 4.38 (m, 1H), 5.10 (d, J=2.5 Hz, 1H), 6.39 (br. s, 1H), 7.46–7.70 (m, 3H), 8.16 (m, 2H); IR (CH$_2$Cl$_2$) 3400–3450 (broad), 3550–3650 (broad), 1775, 1695 cm$^{-1}$, MS (FAB m/e) 220, 185, 160, 159, 135, 120, 105.

EXAMPLE 5

1-phenyl-1-tert-butyldimethylsiloxy-2-benzaldimine a) To a solution of 1-phenyl-2-aminoethanol (5.323 g, 38.80 mmole) in 50 mL dichloromethane was added tert-butyldimethylsilyl chloride (7.030 g, 46.63 mmole) followed, after 15 minutes by tetramethylguanidine (2.430 g, 21.09 mmole). The reaction mixture was stirred at room temperature for 15 minutes and quenched by addition of water (40 mL). Layers were separated. The aqueous phase was extracted with dichloromethane (40 mL). Combined organic phases were washed with brine (2×50 mL), dried over magnesium sulfate and concentrated in vacuo to give crude 2-phenyl-2-tert-butyl dimethylsiloxy-1-ethylamine.

b) 600 g (23.64 mmole) of the compound produced in part (a) herein was mixed with benzaldehyde (2.593 g, 24.46 mmole). After stirring at room temperature for 2 minutes, benzene (50 mL) was added to the reaction mixture. The water liberated was removed by adding magnesium sulfate. The suspension was filtered and the filtrate was concentrated in vacuo. Trace amounts of solvent left were removed under high vacuum. The product, 1-phenyl-1-tert butyldimethylsiloxy-2-benzaldimine, thus obtained was used immediately for the next step.

EXAMPLE 6

(2R,3R)-N-(ethoxyphenylmethyl)-N-(2-oxo-phenylethyl)2,3-oxirane butyramide

To a solution of the compound produced in Example 5 in 15 mL dichloromethane, cooled in a bath at 5° C., was added slowly, (2R,3R)-2,3-oxirane butyryl chloride. Cooling was discontinued after addition and the reaction mixture was stirred for 30 minutes. To this was added triethylamine (2.529 g, 250 mmole) followed, after 2 minutes, by anhydrous ethanol (5.885 g, 128 mmole). After stirring at room temperature for 30 minutes, the reaction mixture was diluted with 50 mL dichloromethane and washed, successively, with saturated sodium bicarbonate solution (50 mL), water (50 mL), and brine (50 mL). The organic phase was dried over magnesium sulfate and concentrated in vacuo to give crude (2R,3R)-N-(ethoxyphenylmethyl)-N-(2-t-butyl dimethyl siloxy-2-phenyl-ethyl) 2,3-oxirane butyramide.

(b) 4.80 g the compound produced in step (a) was dissolved in 12 mL THF and 10 mL of a solution of tetra-n-butylammonium fluoride (1M) in THF was added. The reaction mixture was stirred at room temperature for 12 hours. This was diluted with ethyl acetate (60 mL) and washed with aqueous ammonium chloride (50 mL) and brine (50 mL). The organic phase was dried over magnesium sulfate and concentrated in vacuo. The residue, (2R,3R)-N-(ethoxyphenylmethyl)-N-(2-phenylethan-2-ol)-2,3-oxiranebutyramide was dissolved in 15 mL dichloromethane and a powdered mixture of pyridiniumchlorochromate (8.620 g, 40.0 mmole) and sodium acetate (2.480 g, 30.24 mmole) was added. The reaction mixture was stirred at room temperature for 1.5 hours then diluted with dichloromethane and filtered. The filtrate was concentrated in vacuo and the residue subjected to chromatography on silica gel using 35% ethyl acetate in hexanes to give (2R,3R)-N-(ethoxyphenylmethyl)-N-(2-oxo-2-phenylethyl)2,3-oxirane butyramide.

EXAMPLE 7

(2R,3R)-2,3-oxirane butyryl chloride

To a solution of (2S,3R)-2-bromo-3-hydroxybutyric acid (4.341 g, 23.72 mmole) in 30 mL absolute ethanol, cooled in an ice bath, was added a solution of potassium hydroxide (2.688 g, 49.0 mmole) in 30 mL absolute ethanol. The cooling bath was removed and the suspension was stirred at room temperature for 2 hrs. Solvent was removed in vacuo. To the residue was added THF (50 mL) which was rotary evaporated. This process was repeated twice. The white powder so obtained was dried under high vacuum.

The above material was suspended in 50 mL THF and cooled in a bath at −20° C. To this was added pyridine (1.896 g, 23.97 mmole) followed by thionyl chloride (2.855 g, 24.0 mmole). Cooling was discontinued and the reaction mixture containing the title compound was stirred at room temperature for 2 hrs prior to use.

I claim:

1. A compound represented by the formula

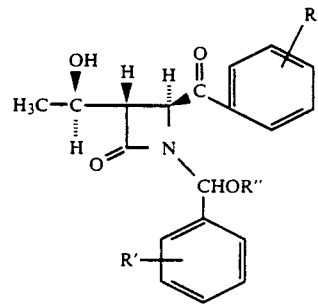

wherein each R' is independently hydrogen, one, two or three of halogen, lower alkyl or lower alkoxy and R" is methyl, ethyl, allyl or a phenyl.

2. A compound of claim 1 wherein each R' is hydrogen and R" is ethyl.

* * * * *